US006831217B1

(12) United States Patent
Matsuoka et al.

(10) Patent No.: US 6,831,217 B1
(45) Date of Patent: Dec. 14, 2004

(54) C3 PLANTS EXPRESSING PHOTOSYNTHETIC ENZYME OF C4 PLANTS

(75) Inventors: Makoto Matsuoka, Nagoya (JP); Mitsue Tokutomi, Tsukuba (JP); Seiichi Toki, Tsukuba (JP); Maurice Sun-Ben Ku, Pullman, WA (US)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 09/003,072

(22) Filed: Jan. 5, 1998

(30) Foreign Application Priority Data

Mar. 11, 1997 (JP) .............................................. 9-056742

(51) Int. Cl.$^7$ ............................ A01H 1/00; A01H 5/00; A01H 5/10; C12N 15/29; C12N 15/82
(52) U.S. Cl. ..................... 800/320.2; 800/278; 800/295; 800/298; 536/23.1; 536/23.2; 536/23.6
(58) Field of Search .................................. 800/278, 298, 800/320.1, 320.2, 295, 300.1, 317.3, 284; 536/23.1, 23.2, 23.6

(56) References Cited

FOREIGN PATENT DOCUMENTS

| DE | 195 31 783 A1 | 3/1997 | ........... C12N/15/82 |
|----|---|---|---|
| JP | WO95/11979 | 5/1995 | ........... C12N/15/60 |
| JP | WO96/01895 | 1/1996 | ........... C12N/15/00 |
| JP | 9-65886 | 3/1997 | ........... C12N/15/09 |

OTHER PUBLICATIONS

Park, Y. et al., The Plant Journal 1996, 9(2) pp. 183–194.*
Matsuoka, M. et al., Mol Gen Genetics 1991, 225:411–419.*
Matsuoka, M. et al., The Plant Journal 1994, 6(3) pp. 311–319.*
Hudspeth, R. et al., Plant Physiology 1992, 98, pp. 458–464.*
Smith et al. Nature Biotechnology, Nov. 1997, vol. 15: pp. 1222–1223.*
Brenner et al. Trends in Genetics, Apr. 1999, vol. 15, No. 4: pp. 132–133.*
Broun et al. Science, Nov. 13, 1998, vol. 282, pp. 1315–1318.*
Ku et al. Plant Physiology 1996, vol. 111, pp. 949–957.*
Luchetta P. et al., Gene 1990, vol. 89, pp. 171–177.*
Metzler M. et al., Plant Molecular Biology 1989, vol. 12 pp. 713–722.*
Rothermel B. et al., J. Biol. Chem. 1989, vol. 264 pp. 19587–19592.*
Marshall J. et al., Plant Physiology 1996, vol. 111, pp. 1251–1261.*
Carvalho et al. The EMBO J. 1992. vol. 11: 2595–2602.*
Kogami et al. Transgenic Research. 1994. vol. 3: 287–296.*
Hiei et al. The Plant Journal. 1994. vol. 6: 271–282.*

Hudspeth et al. Plant Molecular Biology. 1989. vol. 12: 579–589.*
Pathirana et al. Plant Molecular Biology. 1992. vol. 20: 437–450.*
Long D. et al., J. Biol. Chem. 1994, vol. 269, pp. 2827–2833.*
Finnegan P. et al., Plant Mol. Biol. 1995, vol. 27, pp. 365–376.*
Taniguchi M. et al., Eur. J. Biochem. vol. 204, pp. 611–620.*
Taniguchi M. et al., Plant Mol. Biol. 1994, vol. 26, pp. 723–724.*
Sun D. et al., Plant Mol. Biol. 1992, vol. 20, pp. 705–713.*
Pathitana et al. Plant Molecular Biology. 1992. vol. 20: 437–450.*
XP–002074176, Abstract, 1567, Session 62. Transgenics and Biotechnology.
Patent Abstracts of Japan, Publication No. 01086822, publication date Mar. 31, 1989, Application No. 62242610, filed Sep. 29, 1987, Okabe Keiichiro, "Breeding Plants with Suppressed Photorespiration."
Patent Abstracts of Japan, Publication No. 07184657, publication date Jul. 25, 1995, Application No. 05335671, filed Dec. 28, 1993; Ishihara Ho, "C4 Photosynthesis–related gene in rice plant and its promoter", pp. 1–26.
XP–002072320, The Plant Journal (1994) 6(3), pp. 311–319, M. Matsuoka et al., "The promoters of two carboxylases in a C4 plant (maize) direct cell–specific, light–regulated expression in a C3 plant (rice)."
XP–002074175, "Expression of Photosynthetic Genes from C4 Plant in C3 Plants," Matsuoka and Kano–Murakami, N. Murata (ed.), Research in Photosynthesis, vol. III, pp. 879–882.
XP–002072322, Abstract, JO9065886, Phospho Enol Pyruvate Carboxy Kinase Gene Photosynthesis Plant useful to Improve Photosynthesis in Plants.
Kogami, Hiroyuki, et al. (1994) "Molecular and physiological evaluation of transgenic tobacco plants expressing a maize phosphenolpyruvate carboxylase gene under the control of the cauliflower mosaic virus 35s promoter", *Transgenic Research* 3, 287–296.
Ku, Maurice S. B., et al. (1996) "Evolution and Expression of C$_4$ Photosynthesis Genes", *Plant Physiol.* 111:949–957.
Hudspeth, Richard L., et al. (1992) "Expression of Maize Phosphoenolpyruvate Carboxylase in Transgenic Tobacco", *Plant Physiol.* 98:458–464.

(List continued on next page.)

Primary Examiner—David T. Fox
Assistant Examiner—Russell Kallis
(74) Attorney, Agent, or Firm—Townsend and Townsend and Crew LLP

(57) ABSTRACT

A C3 plant has a gene for an enzyme involved in a C4 pathway of photosynthesis and expresses the C4 photosynthesis gene at a high level. More specifically, the C3 plant includes DNA which contains (a) an expression control region of a gene for an enzyme involved in a photosynthetic pathway of a phylogenetically related C4 plant and (b) a structural gene for an enzyme involved in a photosynthetic pathway of the C4 plant. The C3 plant expresses the enzyme encoded by the structural gene at a high level.

18 Claims, 9 Drawing Sheets

OTHER PUBLICATIONS

Matsuoka, Makoto, et al. (1989) "Complete structure of the gene for phosphoenolpyruvate caroboxylase from maize", *Eur. J. Biochem.* 181:593–598.

Matsuoka, Makoto, et al. (1990) "Structure, Genetic Mapping, and Expressing of the Gene for Pyruvate, Orthophosphate Dikinase from Maize", *The Journal of Biological Chemistry*, 265(28):16772–16777.

Rothermel, Beverly A., et al. (1989) "Primary Structure of the Maize NADP–dependent Malic Enzyme", *The Journal of Biological Chemistry*, 264(33):19587–19592.

Nagel, R., et al. (1990) "Electroporation of binary Ti plasmid vector into *Agrobacterium tumefaciens* and *Agrobacterium rhizogenes*", *FEMS Microbiology Letters*, 67:325–238.

Matsuoka, Makoto, et al. (1987) "Classification and Structural Comparison of Full–Length cDNAs for Pathogenesis–Related Proteins", *Plant Physiol.* 85:942–946.

Matsuoka, Makoto, et al. (1989) "Induction of mRNAs for Phosphoenolpyruvate Carboxylase and Pyruvate, Orthophosphate Dikinase in Leaves of a $C_3$ Plant Exposed to Light", *Plant Cell Physiol.* 30(4):479–486.

Jefferson, Richard A., et al. "GUS fusions: β–glucuronidase as a sensitive and versatile gene fusion marker in higher plants", *The EMBO Journal*, 6(13):3901–3907.

Ohta, Shozo, et al. (1990) "Construction and Expression in Tobacco of a β–Glucuronidase (GUS) Report Gene Containing an Intron Within the Coding Sequence", *Plant Cell Physiol*, 31(6):805–813.

Chilton, Mary–Dell, et al. (1974) "*Agrobacterium tumefaciens* DNA and PS8 Bacteriophase DNA Not Detected in Crown Gall Tumors", *Proc. Nat. Acad. Sci USA*, 71(9):3672–3676.

Hiei, Yukoh, et al. (1994) "Efficient transformation of rice (*Oryza sativa* L.) mediated by Agrobacterium and sequence analysis of the boundaries of the T–DNA", *The Plant Journal* 6(2):271–282.

Edwards, Gerald E., et al. (1988) "$C_4$ Photosynthesis: Activities of Photosynthetic Enzymes in a Virescent Mutant of Maize Having a Low–temperature–induced Chloroplast Ribosome Deficiency", *Aust. J. Plant. Physiol*, 15:385–395.

Matsuoka, Makoto (1995) "The Gene for Pyruvate, Orthophosphate Dikinase in C4 Plants: Structure, Regulation and Evolution", *Plant Cell Physiol*, 36(6):937–943.

Gehlen, Johanna, et al. (1996) "Effects of altered phosphoenolpyruvate carboxylase activities on transgenic C3 plant *Solanum tuberosum*", *Plant Molecular Biology* 32:831–848.

Hatch, M.D., "Photosynthesis: The Path of Carbon," *Plant Biochemistry*, Third Ed., Academic Press, Ch. 24, pp. 797 and 809–818 (1976).

Burnell, et al., "Photosynthesis in Phosphoenolpyruvate Carboxykinase–Type $C_4$ Plants: Photosynthetic Activities of Isolated Bundle Sheath Cells," *Archives of Biochemistry and Biophysics*, 260(1):177–186 (Jan. 1988).

Matsuoka, et al., "Expression of photosynthetic genes from the $C_4$ plant maize, in tobacco," *Mol. Gen. Genet.*, 225:411–419 (1991).

Matsuoka, et al., "Tissue–specific light–regulated expression directed by the promoter of a $C_4$ gene, maize pyruvate, orthophosphate dikinase, in a $C_3$ plant, rice," *Proc. Natl. Acad. Sci. USA*, 90:9586–9580, (ctober 1993).

Matsuoka, et al., "The promoters of two carboxylase in a $C_4$ plant (maize) direct cell–specific, light–regulated expression in a $C_3$ plant (rice)," *The Plant Journal*, 6(3):311–319 (1994).

Matsuoka, et al., "Molecular Engineering of $C_4$ Photosynthesis," *Annu. Rev. Plant Physiol. Plant Mol. Biol.*, 52:297–314 (2001).

* cited by examiner

FIG. 2A

```
                                                        tctagagatgta      -1201
atggtgttaggacacgtggttagctactaatataaatgtaagtcaaaattcgatgttatttctatttcacttacc  -1121
tagcattatctcattctaattgtgtgataacaaatgcattagaccataattctgtaaatacgtacattaagcacacag  -1041
tctatattttaaaattcttcttttgtgtggatatcccaaccaaatctttgttggttgtgcacgtgtatcttcaccg   -961
ctgccaagtgccaacaacacgcatcgtcgtgcaaatctttgttgttgtgcacgtcggcgccaatggaggagacacct  -881
gtacggtgccctggcatcataccaagaattaaatatactttttcttgaacacacagtctcgtagatggcaccctatcctacaata  -801
gccatgtattgcatcataccaagaattaaatatactttttcttgaaccacacagttattatagcgcacttcttgttctgg   -721
ttgaacacttattggaacaataaaatcccgagttcctaaccacagttcacttttttt[cctaatcc]cctagaaacta  -641
aatttaaattcataaatttaatgaaatgttaatgaaaacaaaaaattatctacaaagactcttcctccgatgcagccta  -561
cctcactgcaacagacgccctctccacatcctg̲caaaagcattcctccaagattcctgcgatccccgaatccagcattaactgc  -481
cttgctaacaagacgccctctccacatcctg̲ctaccaattagcacaagaataacaagaaggcaggtgagcagtgacaaagca   -401
taaggagcgcaacagagccagcagccagcagcaaggagcaagccaagcagccagctctccagttcccagttccccttg  -321
cgtcaacagagccagcagtagcagacacacccctcgcctctccacatgccgctaacagcagcaagcaaggccgcctttccaaaacgccgagggccgcc  -241
cgattgccgccacagccggttcggttgcggttacgccgccaacgactccccatccg̲[tattt]gaacccaccccgcgactgcattg  -161
cctcagcagccacacacacacaccgccgccacacccgccgccggccacccgccgccggccg   -81
cgttcccgtgcacagcacacacacaccgccgccacacccgccgccggccacccgccgccggccg    -1
                    exon 1/intron 1
atcaccaatcgcatcgcagcagcagcgagcagcgccgctccaaccgtctcgctccctgcttagcttcccgcccg      80
    START
cgcc ATGGCGTCGACGAAGGCACCAAGGCACCAAGGCACCACTCCATGACGCGGAGAAGCACCACTCCATGACGCGGAGAAGCAGTCCGTCGGTCCCAG    160
GCAAGGTCTCCGAGGACGACAAGCTCATCGAGTACGAGTCATCGATGCCGCTTCCTCCAACATCCTCCAGGACCTC     240
CACGGGCCTTCGCGGCCTTCGCGGCCAATT/gtaactaaccaccgccgccatttcttcttcgaccggttgccgcctgcgcgcg    320
             exon 1/intron 1
```

FIG. 2B

```
gcactgctcgtgtcgtgtgcttagtgtcttactactgtaatgcatgcag/GTCCAGGAGTGCTACGAGGTGTCGGC      400
                                          intron 1/exon 2
CGACTATGAGGGCAAAGGAGACACGACGAAGCTGGGCGAGCTCGGCCAAGCTCACGGGCGCTGGCCCCCGACGCCA      480
TCCTCGTGGGCGAGCTCCATCCTGCACATGTCAACCTGCCCAACCTGGCCGAGGAGCTGCAGATCGCGCACCGCCGC    560
AACAGCAAGCTCAAGAGAAAGGTGGGTTCGCCGACGAGGGCTCCGACGAGTCCGACACATCGAGGAGACGCTCAAGCG   640
CCTCGTGTCCGAGGTCGGCAAGTCCCCCGAGGAGGTGTTCGAGGCGCTCAAGAACCAGACCGTCGACCTCGTCTTCACCG 720
CGCATCCCACGCAGTCCGCCCCGCCGCTCGCTCCTGCAGAAAAACGCCAG/gtatatatttctcaatggcttgatcgatatg 800
                                          exon 2/intron 2
ctactcacgttatacccttaagtcttaaccattattatttttgataaataaaaatgtcggtcttgtcgctgcag/G      880
                                                                intron 2/exon 3
ATCCGGAATTGTCTGACCCAGCTGAATGCCAAGGACATCACTGACGACGACAAGCAGGAGCTCGATGAGGCTCTGCAGAG 960
AGAG/gtacgtacatattacattcacaccaggaatgcaagaacttatcagagagacattcattctttgatagagataga   1040
exon 3/intron 3
atagaacacatgcacagtacacgtgactcatgagcttgcaagacatcgagcacgtaagttagtgcgcagag           1120
aaatcttcaattatatgtcaagtcaggtcaggttctcccattaaaacacatataaataaatattcattattatcaagct   1200
aagtaataaacaaccaaactttccactattccaaactgtctttaaactgtcttgcaaagtagaaactaatcaggaaa     1280
gaactagactgcacattgtttaacaatgcaatgaagactgtactacactgaattatttatatgctattctccagctgtgct 1360
acttgacttaagattcaatgttgaagacacctgatgaaaactcatttgtacaaagatctcttactcatagacattgagtagaactt 1440
caaagcattcctttacttaaaaagatcatttgttagttgttactcatcatcattatttttcctaacaagtagggcat    1520
cggtaccacagatgcattaatgaggaatcaaacctagacctaactccacaccctcaattgctaggctatgctcaagttcc  1600
ccagtttctccttgatgagacgagtttcatctgtcatcatgtcatcatcgagcactcggtaaagagcgtctctcatgtgcatatata 1680
tagtgttacaaatttcagacgagttacactgctttactactgactctactactcactcggtaaagagcgtctctcatgtgcatatata 1760
tgatgcagaccactgagaagtttactgcttcaagccaccaaagtggtattttttgttgttgtttagttctaatt        1840
```

FIG. 3A

```
cctttcttggtgttcacag/ATCCAAGCAGCCTTCAGAACCGATGAAATCAGGAGGGCACAACCCACCCCCAGGACGA  1920
                   intron 3/exon 4
AATGGCGCTATGGGATGAGCTACATCCATGAGACTGTATGGAAGGGCCTGCCTAAGTTCTTGCGCCGTGTGGATACAGCCC  2000
TGAAGAATATCGGCATCAATGAGCGCCCTTCCTACAATGTTTCTCTACAATGTTCTCGGTTCTCTCTTGGATGGGTGACCGC  2080
GATG/gtacatttctgcctaccccttttcaataaagtggcaggagctctcgtcttcagcttgagagaaccttcctgctt  2160
exon 4/intron 4
tactctgactgcaatagatgttcagaaaaactagtctatcatttcgagctctcaggagctagaatttaaaaattgaaatt  2240
attagtacacctcactaataaaatttatcatcatgctagcacacataagcatataattaatcaaatcttta  2320
tattgcaacctgaacctaacttgtgaattttttatatcacagaattatacgtgtagtattatttatatcaaagag  2400
tgcttatattatatcagtactgtcctgtcaatattcaaggctaacgttttctttctcgccagaaaattatatataca  2480
gaattatatatgttttttctaagcctgtatatctttgcaatctatcgctatatag/GAAATCCAAGAGTTACCCGGAGGTGA  2560
                                                        intron 4/exon 5
CAAGAGATGTATGCTTGCTGGCCAGAATGATGCTGCAAACTTGTACATCGATCAGATTGAAGAGCTGATGTTTGAG/gta  2640
                                                                         exon 5/intron 5
ctgtacatccatactgcagatttgtttgattgaatgctctatgatttttgcttgccctgttttttgctgtctccggtcc  2720
ataccagaactctcatgcatcatgcatcgtctgatatatctgtag/CTCTCTATGTGGCGCTGCAACGATGAGCTTCGTTCG  2800
                                              intron 5/exon 6
TGCCGAAGAGCTCCACAGTTCGTCTGGTTCGTCCAAAGTTACCAAGTATTACATAG/gtaaccacaaacagaagcatttatgtt  2880
                                                         exon 6/intron 6
tgcttaattttgcctgccgcgtacaggcttttgcaaaagtctccactagtgttttcaaattaattgaggctctttttggc  2960
atcttttctgaagtgtatttgctggccgcag/AATTCTGGAAGCAAATTCCTCCAAACGAGCCCTACCGGGTGATACTAGGC  3040
                                intron 6/exon 7
```

FIG. 3B

```
CATGTAAGGGACAAGCTGTACAACACGCGAGCGTGCTCGCCATCTGCTGGCTTCTGGAGTTTCTGAAATTTCAGCGGA    3120
ATCGTCATTTACCAGTATCGAAGAG/gtaaatatcgtcatgtatatattatatattcatagtatgacatcagcactgca    3200
                       exon 7/intron 7
actaacaaaaaaaatcactactgtcgtgcatgcag/TTCCTTGAGCCACTTGAGCTGTGCTACAAATCACTGTGT    3280
                 intron 7/exon 8
GACTGCGGGCGACAAGGCCATCGCGGACGGGAGCCTCCTGACCTCGGCCAGTTTCACGTTCGGGCTCTCCCTGGT    3360
GAAGCTGGACATCCGGCAGGAGTCGGAGCGGCGGAGCGGCACCGACGTGATCGACGCCATCACCACGCCACCTCGT    3440
ACCGCGAGTGGTCCGAGGACGGGCAGGAGTGGCTGTGTGCGCAGGCAAGCGCCCCGCTGTGCCCCCGGAC    3520
CTTCCCCAGACCGGAGGAGATCGCCGACGTCATCGCGGCGTCCCACGTCCCGCCCGAGCTCCCGACAGCTTCGGCCC    3600
CTACATCATCTCCATGGCCGCGACGGCCCCCCTCGGAGCTCCTCGCCCGTGGAGCGCCTCTTCTCGGCCAG    3680
CCGTGCCCGTGGTGCCGCTGTTCGAAAGGCTGGCCAGCCTGGCCCGTCGGCCGCGTCCGACTCGGCTACTCCGACTCGGTG    3760
GACTGGTACATGGACCGGATCAAGGGCAAGCAGCAGGTCATGTCGGCCAAGGACGCCGGCCGCCT    3840
GTCCGCGGCCGTGTACAGGGCAGCTGTACAGGGGTGGCGCAGTGGCCCACCTTGCCATCCGTGTCCAGCGCCACCTTGT    3920
TCCACGGCCGCGGAGGCACCGTGGGCAGGGCGAGGTCATGCGAGGTCTGAGTTCTGTTCTCGGGGGAGGAGCACCTGCTTCGGGACACCATC    4000
AACGGGTCCATCCGTGTGACGGTGCAGGGCGAGGTGCAGGGCCACGCGGATGCACCCGGAGACCCGGAGTTCCAGACTCT    4080
GCAGCGCTTCACGGCCCACGGGCCGCCACGCTGGAGCACGGACATGCACCCCCGGTCTCTCCCCAAGCCCGAGTGGCCGCAAGCTCATGG    4160
ACGAGATGGGCGGTCGTGGCCACGAGGAGTACCGCTCCGTCGTCAAGGAGGCGCGCTTCGTCGAGTACTTCAGATCG/    4240
                                                                          exon 8/
```

FIG. 4

```
gtatgctgcattgccattgctttgtgacgatcgaattcatccatgtcgatcgttcttttcattcattcgagcgtttgt    4320
intron 8
gcgtcactcactatcag/GCTACACCGGAGACCGAGTACGGGAGGATGAACATCGGCAGCCGGCCAAGAGGAGGCCC    4400
    intron 8/exon 9
GGCGGGCGCATCACGACCCTGCGCGCCATCCCCCTGGATCTTCTCGTGGACCCAGACCAGGTTCCACCTCCCCGTGTGGCT    4480
GGGAGTCGGGCCCGCATTCAAGTTCGCCATCGACAAGGACGTCAGGAACTTCCAGGTCCTCAAAGAGATGTACAACGAGT    4560
GGCCATTCTTCAGGTCACACCCTGCTGGAGATGGTTTTCGCCAAGGAGACCCCGGCATTGCCGGCTTGTATGAC    4640
GAGCTGCTTGTGCCAGAAGAACTCAAGCCCTTTGGGAAGCAGCTCAGGGACACTGGGAGACACAGCAGCTTCTCCT    4720
CCAG/gtaccaaaaccagcactgcactgtacgatatgaatagaataaaagtctgttgtctggctcctgatcgatgactactc    4800
exon 9/intron 9
cattttgtgcag/ATCGCTGGGCACAAGGATATTCTTGAAGGCGATCCATTCCTGAAGCAGGACTGGTGCTGCGCAACCC    4880
    intron 9/exon 10
CTACATCACCACCCTGAACGTGTTCCAGGCCTACACGCTGAAGCGGATAAGGGACCCCAACTTCAAGGTGACGCCCCAGC    4960
CGCCGCTGTCCAAGGAGTTCGCCGACGAGAACAAGCCCGGCCGACTGGTCAAGCTGAACCGGAGCGAGTACCCGCCC    5040
GGCCTGGAAGACACGCTCATCCTCACCATGAAGGGGCATCGCGCCGGCATGCAGAACACTGGCTAG gcggcttctcttca    5120
                                                          STOP
ctcacctgcagagtgcagagtgcaccgcaataatcagcttccggatgtgcgcgttttgtcagttttgatgaaatgccgaactggc    5200
agcgtctgttttcctatgcatatgtaattcctgcctcttttatattcactcttgttgtcaagtccaagtgaaaatct    5280
ggcatattatacatattgtaataaacatcgtacaatctgcatgctgttttgtaataattaatatccagccca    5360
ttggatggacttgtttaccatggtgttacttcagccacctctcttagttgtgctaaacatttctgattggtattttt    5440
ttattagagtaacctagtgcattacttagtagatatctagtggcactagtgattagtttgcaagattgagaact    5520
tgttactcgctcctagaggttaacactagcagcaagtgattgattggagcttaggg
```

C3 PLANTS EXPRESSING PHOTOSYNTHETIC ENZYME OF C4 PLANTS

BACKGROUND OF THE INVENTION

1. Field of the Invention

The present invention relates to a C3 plant which contains a gene for an enzyme involved in a C4 pathway of photosynthesis (hereinafter, referred to as a C4 photosynthesis gene) and expresses the C4 photosynthesis gene at a high level.

2. Description of the Related Art

Plants are classified into C3 plants, C4 plants, and crassulacean acid metabolism (CAM) plants, based on the kind of initial fixed products in photosynthetic fixation of $CO_2$. Ninety percent or more of plants on the earth belong to C3 plants, which include, for example, agriculturally important plants such as rice and barley. The photosynthetic pathway of C3 plants is also called the Calvin pathway, and an enzyme involved in photosynthetic fixation of $CO_2$ in this pathway is ribulose-1,5-bisphosphate carboxylase. This enzyme has a low affinity for $CO_2$ and has a high affinity for $O_2$. Therefore, the efficiency of a photosynthetic reaction as well as photosynthetic fixation of $CO_2$ is low in the C3 photosynthetic pathway.

The C4 plants are those which have evolved so as to overcome such non-efficient photosynthetic fixation of $CO_2$. The C4 plants have a mechanism for concentrating $CO_2$ and a high photosynthetic capacity. An enzyme involved in photosynthetic fixation of $CO_2$ in the photosynthetic pathway of the C4 plants is phosphoenolpyruvate carboxylase. This enzyme has a high capacity of photosynthetic fixation of $CO_2$ without its activity being inhibited by $O_2$.

CAM plants have a photosynthetic system suitable for dry environment, and the photosynthetic system is considered to be a sort of evolved form of the C3 photosynthetic system.

It is expected that the photosynthetic capacity and productivity of the agriculturally important C3 plants (e.g., rice) will be remarkably improved by providing a C3 plant with the photosynthetic function of a C4 plant. Some attempts have been made to introduce a C4 photosynthesis gene into a C3 plant.

In order to express a photosynthesis gene of a C4 plant, a chlorophyll a/b binding protein promoter or a Cauliflower mosaic virus (CaMV) 35S promoter linked thereto has been used. For example, there is a report by Kogami et al., Transgenic Research 3: 287–296 (1994): The (CaMV) 35S promoter which can be expressed at a high level in a leaf tissue of a C3 plant was linked to a photosynthesis gene of a C4 plant (the phosphoenolpyruvate carboxylase (PEPC) gene) to produce recombinant DNA, and then the recombinant DNA was introduced into a C3 plant, tobacco; however, the PEPC activity in the C3 plant merely increased by 2 to 3 times at most. There is another report by Matsuoka et al., Plant Physiol. 111: 949–957 (1996): For the purpose of studying the function of a promoter of the C4 photosynthesis gene, a fusion gene of the β-glucuronidase (GUS) gene from *E. coli* and a 5'-flanking region (promoter region) of the PEPC gene was introduced into tobacco, whereby the GUS gene was expressed at a high level. There is also a report by Hudspeth et al., Plant Physiol. 98:458–464 (1992): As a C4 photosynthesis gene, the PEPC genome gene of maize containing the expression control region (promoter region) was introduced into tobacco; however, the PEPC activity merely increased by 2 to 3 times.

Thus, to the extent that the inventors are aware of, prior to the filing of Japanese Patent application No. 9-56742, on which the present application claims priority, there were no reports on examples where an enzyme involved in photosynthesis was expressed at a high level. Accordingly, there is a demand for techniques of expressing a photosynthesis gene of a C4 plant in a C3 plant at a high level, thereby enhancing the photosynthetic capacity of the C3 plant.

SUMMARY OF THE INVENTION

The present invention intends to overcome the above-mentioned problems, and its objective is to express a photosynthesis gene of a C4 plant in a C3 plant at a high level.

As described above, there is an example in which attempts have been made to introduce a PEPC genome gene involved in a photosynthetic pathway of a C4 plant, maize (poaceae) into a C3 plant, tobacco (solanaceae), resulting in low expression efficiency. The inventors of the present invention found that by introducing a gene containing (a) an expression control region of an enzyme involved in photosynthetic pathway of a C4 plant which is phylogenetically related to a C3 plant and (b) a structural gene for an enzyme involved in a photosynthetic pathway of a C4 plant which is phylogenetically related to a C3 plant, into the C3 plant, the expression efficiency of the enzyme involved in the C4 pathway of photosynthesis is remarkably enhanced, thereby achieving the present invention.

A C3 plant expressing a gene of a phylogenetically related C4 plant according to the present invention includes DNA containing (a) an expression control region of a gene for an enzyme involved in a photosynthetic pathway of a phylogenetically related C4 plant and (b) a structural gene for an enzyme involved in a photosynthetic pathway of the C4 plant, wherein the C3 plant expresses the enzyme encoded by the structural gene at a high level.

A method for producing a C3 plant which expresses a gene of a phylogenetically related C4 plant according to the present invention includes the steps of: transforming cells of the C3 plant with DNA containing (a) an expression control region of a gene for an enzyme involved in a photosynthetic pathway of a phylogenetically related C4 plant and (b) a structural gene for an enzyme involved in a photosynthetic pathway of the C4 plant; and regenerating the transformed cells of the C3 plant into the C3 plant; wherein the regenerated C3 plant expresses the enzyme encoded by the structural gene at a high level.

In one embodiment of the present invention, the C4 plant is a monocotyledonous plant, and the C3 plant is a monocotyledonous plant.

In another embodiment of the present invention, the C4 plant is a dicotyledonous plant, and the C3 plant is a dicotyledonous plant.

In another embodiment of the present invention, the DNA is a genome gene of the C4 plant.

In another embodiment of the present invention, the genome gene of the C4 plant is a genome gene of a C4 poaceous plant, and the C3 plant is a C3 poaceous plant.

In another embodiment of the present invention, the genome gene of the C4 poaceous plant is a genome gene for phosphoenolpyruvate carboxylase from maize, and the C3 poaceous plant is rice.

The present invention also relates to a C3 plant obtainable by a method according to the present invention, and a portion of the C3 plant.

In one embodiment of the present invention, the portion of a C3 plant according to the present invention is a vegetable.

In another embodiment of the present invention, the portion of a C3 plant according to the present invention is a fruit.

In another embodiment of the present invention, the portion of a C3 plant according to the present invention is a flower.

In another embodiment of the present invention, the portion of a C3 plant according to the present invention is a seed.

A C3 plant tissue expressing a gene of a phylogenetically related C4 plant according to the present invention includes DNA containing (a) an expression control region of a gene for an enzyme involved in a photosynthetic pathway of a phylogenetically related C4 plant and (b) a structural gene for an enzyme involved in a photosynthetic pathway of the C4 plant, wherein the C3 plant tissue expresses the enzyme encoded by the structural gene at a high level.

A method for producing a C3 plant tissue which expresses a gene of a phylogenetically related C4 plant according to the present invention includes the steps of: transforming cells of the C3 plant with DNA containing (a) an expression control region of a gene for an enzyme involved in a photosynthetic pathway of a phylogenetically related C4 plant and (b) a structural gene for an enzyme involved in a photosynthetic pathway of the C4 plant; and regenerating the transformed cells of the C3 plant into the C3 plant tissue; wherein the regenerated C3 plant tissue expresses the enzyme encoded by the structural gene at a high level.

In one embodiment of the present invention, the C4 plant is a monocotyledonous plant, and the C3 plant tissue is a tissue of a monocotyledonous plant.

In another embodiment of the present invention, the C4 plant is a dicotyledonous plant, and the C3 plant tissue is a tissue of a dicotyledonous plant.

In another embodiment of the present invention, the DNA is a genome gene of the C4 plant.

In another embodiment of the present invention, the genome gene of the C4 plant is a genome gene of a C4 poaceous plant, and the C3 plant tissue is a tissue of a C3 poaceous plant.

In another embodiment of the present invention, the genome gene of the C4 poaceous plant is a genome gene for phosphoenolpyruvate carboxylase from maize, and the C3 poaceous plant is rice.

A C3 plant seed expressing a gene of a phylogenetically related C4 plant according to the present invention includes DNA containing (a) an expression control region of a gene for an enzyme involved in a photosynthetic pathway of a phylogenetically related C4 plant and (b) a structural gene for an enzyme involved in a photosynthetic pathway of the C4 plant, wherein the C3 plant seed expresses, at least upon germination and growing, the enzyme encoded by the structural gene at a high level.

A method for producing a C3 plant seed which expresses a gene of a phylogenetically related C4 plant according to the present invention includes the steps of: transforming cells of the C3 plant with DNA containing (a) an expression control region of a gene for an enzyme involved in a photosynthetic pathway of a phylogenetically related C4 plant and (b) a structural gene for an enzyme involved in a photosynthetic pathway of the C4 plant; regenerating the transformed cells of the C3 plant into the C3 plant; and obtaining a seed from the C3 plant; wherein the C3 plant seed expresses, at least upon germination and growing, the enzyme encoded by the structural gene at a high level.

In one embodiment of the present invention, the C4 plant is a monocotyledonous plant, and the C3 plant seed is a seed of a monocotyledonous plant.

In another embodiment of the present invention, the C4 plant is a dicotyledonous plant, and the C3 plant seed is a seed of a dicotyledonous plant.

In another embodiment of the present invention, the DNA is a genome gene of the C4 plant.

In another embodiment of the present invention, the genome gene of the C4 plant is a genome gene of a C4 poaceous plant, and the C3 plant is a C3 poaceous plant.

In another embodiment of the present invention, the genome gene of the C4 poaceous plant is a genome gene for phosphoenolpyruvate carboxylase from maize, and the C3 poaceous plant is rice.

Thus, the invention described herein makes possible the advantages of (1) providing a C3 plant as well as a tissue and a seed thereof which express a C4 photosynthetic gene efficiently, and (2) further providing a technical foundation for enhancing the photosynthetic capacity of a C3 plant by conferring the C4 photosynthetic capacity to the C3 plant.

These and other advantages of the present invention will become apparent to those skilled in the art upon reading and understanding the following detailed description with reference to the accompanying figures.

BRIEF DESCRIPTION OF THE DRAWINGS

FIGS. 2A and 2B are diagrams showing a base sequence of about 8 Kb of a DNA fragment including the PEPC gene.

FIG. 3A and 3B are a continuation from FIG. 2B.

FIG. 4 is a continuation from FIG. 3B.

DESCRIPTION OF THE PREFERRED EMBODIMENTS

Figure 1:
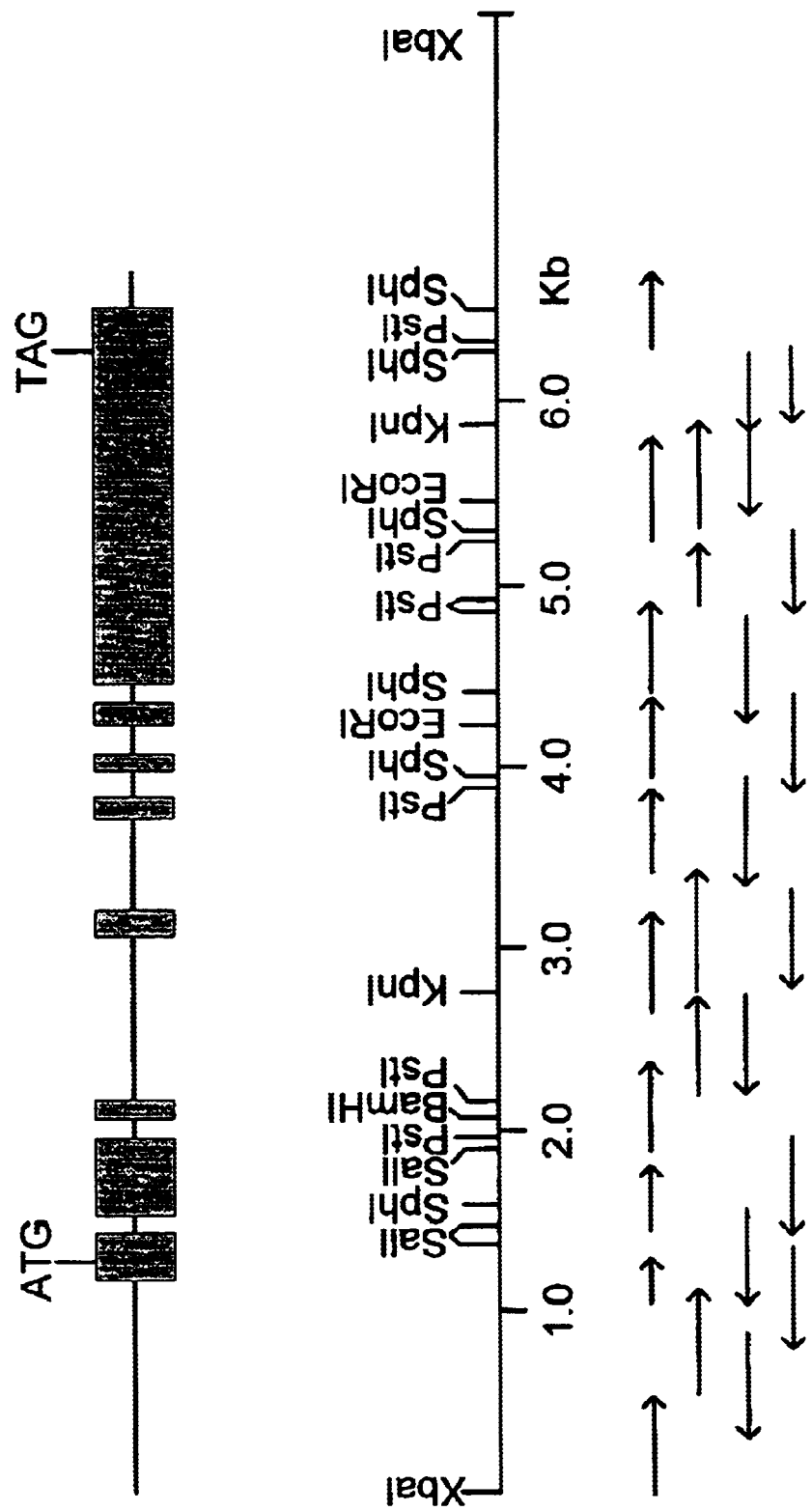
FIG. 1 is a diagram showing a restriction enzyme map of a DNA fragment including the PEPC gene, where wider portions of the lines represent exons.

The present invention will be described by way of illustrative examples with reference to the drawings.

Definitions

The term "phylogenetically related" used herein refers to having some phylogenetic relatedness, e.g., belonging to the same family, the same order, or the same class.

The term "plants" as used herein includes, unless indicated otherwise, plant bodies, plant organs, plant tissues, plant cells, and seeds. An example of a plant cell includes callus. An example of a plant organ includes a root, a leaf, a flower and the like.

The term "C3 plants" refers to plants which fix $CO_2$ in a C3 pathway of photosynthesis, including monocotyledonous plants such as rice, wheat, and barley, as well as dicotyledonous plants such as soybeans, potatoes, and sweet potatoes.

The term "C4 plants" refers to plants which fix $CO_2$ in the C4 pathway of photosynthesis, including monocotyledonous plants such as maize, sugarcane, and sorghum, as well as dicotyledonous plants such as Flaveria, and Amaranthus.

The term "enzyme involved in a C4 pathway of photosynthesis" refers to an enzyme involved in photosynthesis of C4 plants. Although not limited thereto, the enzyme includes, for example, carbonic anhydrase (CA), phosphoenolpyruvate carboxylase (PEPC), pyruvate, orthophosphate dikinase (PPDK), malate dehydrogenase (MDH), malic enzyme, alanine oxaloacetate aminotransferase, phosphoenolpyruvate carboxykinase (PEPCK). Expression control regions of genes for these enzymes and structural genes for these enzymes can be used in the present invention.

In connection with the expression of an enzyme, the term "at a high level" as used herein refers to the specific activity (activity per unit protein mass) of an enzyme in a crude extract of a green leaf of the C3 plant after introduction of a gene for the enzyme involved in a C4 pathway of photosynthesis into a C3 plant, is at least 7 times the specific activity of the enzyme in the C3 plant before the introducing the gene. The specific activity is preferably at least 10 times, more preferably at least 40 times, still more preferably at least 75 times, and most preferably at least 100 times.

The term "expression control region" as used herein refers to a region containing a sequence controlling the expression of a structural gene. Although not limited thereto, the expression control region includes, for example, a transcriptional control sequence, a post-transcriptional control sequence, and/or a transcription termination sequence. Introns also correspond to the expression control region.

Examples of the "transcriptional control sequence" include some sequences such as a promoter, a repressor, an activator, and an enhancer. The "post-transcriptional control sequence" includes elements involved in a primary transcript being subjected to post-transcriptional processing (e.g., addition of poly A, generation of a cap structure, splicing, etc.). The "transcription termination sequence" includes elements involved in termination of transcription such as a terminator. These expression control regions can be positioned separately upstream or downstream of a structural gene, depending upon the properties thereof.

The term "DNA containing an expression control region of a gene for an enzyme involved in a C4 pathway of photosynthesis and a structural gene for an enzyme involved in a C4 pathway of photosynthesis" refers to a recombinant DNA sequence containing an expression control region and a structural gene for an enzyme, a genome gene sequence containing an expression control region and a structural gene for an enzyme, or an expression vector containing the recombinant DNA sequence or the genome gene sequence. This DNA also includes chemically synthesized DNA.

The structural gene includes DNA (which may include introns) encoding the protein portion of an enzyme, and cDNA from mRNA.

The expression vector refers to a nucleic acid sequence in which the "DNA containing an expression control region of a gene for an enzyme involved in a C4 pathway of photosynthesis and a structural gene for an enzyme involved in a C4 pathway of photosynthesis" is introduced and linked to be operable in a host cell. The expression vector may include an expression control sequence (e.g., various regulator elements such as a promoter, an enhancer, and a terminator) other than the expression control region of a gene for an enzyme involved in a C4 pathway of photosynthesis. The expression control sequence can be used for controlling an expression of the structural gene. (Isolation of an expression control region of a gene for an enzyme involved in a C4 pathway of photosynthesis and a structural gene for an enzyme involved in a C4 pathway of photosynthesis)

According to the present invention, a C4 plant and a C3 plant which are phylogenetically related to each other are used. Preferably, in the case of using a gene of a C4 monocotyledonous plant, the gene is introduced into a C3 monocotyledonous plant, and in the case of using a gene of a C4 dicotyledonous plant, the gene is introduced into a C3 dicotyledonous plant. More preferably, the C4 plant and the C3 plant belong to the same family.

The structural gene for an enzyme involved in a C4 pathway of photosynthesis can be isolated by a well-known method. mRNA which is a transcript of the structural gene for the enzyme is isolated, and cDNA is produced using the isolated mRNA. Genome DNA is screened by using the cDNA, whereby an expression control region of the enzyme can be obtained. About 8 Kb of a genome gene fragment containing PEPC gene of maize has already been isolated (Eur. J. Biochem. 181: 593–598, 1989). The genome gene fragment includes upstream and downstream regions of the PEPC structural gene and introns (i.e., an expression control region), so that it can be used as it is.

Another gene involved in the C4 pathway of photosynthesis, the PPDK genome gene (maize) has also been isolated (Matsuoka et al., J. Biol. Chem. 265: 16772–16777 (1990)), which can be used in the present invention. An expression control region of the PPDK genome gene has similarity to that of the PEPC genome gene, and this expression control region can be used in the present invention. Furthermore, a genome gene for the NADP-malic enzyme has also been isolated (Rothermel et al., J. Biol. Chem. 264: 19587–19592, 1989), and an expression control region and a structural gene of this genome gene can be used in the present invention.

By using an expression control region of a gene for any enzyme involved in a C4 pathway of photosynthesis, a structural gene for any enzyme involved in a C4 pathway of photosynthesis may be expressed. The enzyme includes carbonic anhydrase (CA), phosphoenolpyruvate carboxylase (PEPC), pyruvate, orthophosphate dikinase (PPDK), malate dehydrogenase (MDH), malic enzyme, alanine oxaloacetate aminotransferase, phosphoenolpyruvate carboxykinase (PEPCK), and the like.

Structural genes of malate dehydrogenase or alanine-oxaloacetate aminotransferase can be isolated by the following method well known to those skilled in the art, comprising the steps of: isolating and purifying any of these enzymes; sequencing a part of an amino acid sequence of the enzyme; preparing a probe based on a deduced nucleotide sequence from the determined amino acid sequence; and screening a cDNA library or genome library using the probe. Expression control regions of these enzymes can also be used in the present invention. If the resulting genome gene encoding an enzyme include an expression control region and a structural gene, the genome gene can be used as it is. The expression control region of a gene for an enzyme involved in the C4 pathway of photosynthesis can be determined in comparison with the sequence of an expression region of another plant gene.

A recombinant gene containing an expression control region and a structural gene for an enzyme involved in the C4 pathway of photosynthesis can be produced by a method well known to those skilled in the art. The recombinant gene can have a plurality of expression control regions and/or structural genes.

The resulting genome gene for an enzyme involved in a C4 pathway of photosynthesis or the recombinant DNA sequence obtained as described above can be used for transformation of the C3 plant as it is or in the form of an expression vector. Two or more recombinant DNA sequences or genome genes may be incorporated into the C3 plant. By introducing two or more genes which are involved in a C4 pathway of photosynthesis into a C3 plant, it is expected that a photosynthetic capacity is further improved.

Construction of an Expression Vector

It is known to those skilled in the art that a vector for constructing an expression vector can be selected depending upon the purpose of expression and the host cell. A start vector can preferably include a promotor, an enhancer, a T-DNA region, and a drug resistant gene.

The vector used for constructing the expression vector of the present invention does not necessarily require an additional promoter for expressing a structural gene of the C4 plant. This is because an expression control region (e.g., promoter) of the phylogenetically related C4 plant is considered to function in an expression control system of the C3 plant. However, it may be desirable that the expression vector used in the present invention has an expression control region. Although not limited thereto, examples of the promoter in this case include a promoter whose expression is induced by a certain stress such as an infection specific protein PR1a of tobacco, a CaMV 35S promoter, and a promoter of nopaline synthase (NOS).

An enhancer can be used for expression at a high level. As the enhancer, an enhancer region containing a sequence upstream of the above-mentioned CaMV 35S promoter is preferable. A plurality of enhancers can be used.

A terminator can also be used. Although not limited thereto, examples of the terminator include a CaMV 35S terminator, a terminator of nopaline synthase (TNOS), and a terminator of a tobacco PR1a gene.

It is desirable to use a drug resistant gene which allows a transformed plant to be easily selected. The neomycin phosphotransferase II (NPTII) gene, the hygromycine phosphotransferase (HPT) gene, and the like can be preferably used. Although not limited thereto, examples of the promoter expressing the drug resistant gene include the above-mentioned plant gene promoters. Preferably, the CaMV 35S promotor which is constitutively expressed at a high level can be used. The NPTII gene is useful to detect transformants or transformed cells. The HPT gene is expressed when introduced into a nuclear genome of a plant, and the plant becomes resistant to hygromycine, whereby the introduction of the gene into the nuclear genome is confirmed.

As a start vector used in the present invention for constructing an expression vector, a pBI-type vector, a pUC-type vector, or a pTRA-type vector can be preferably used. The pBI-type binary vector can be more preferably used. This vector contains a gene in a region (T-region) to be introduced into a plant and the NPTII gene (providing kanamycin resistance) expressed under the control of a plant promoter as a marker gene. The pBI-type vector can introduce the gene of interest into a plant via Agrobacterium. Examples of the pBI-type vector include pBI121, pBI101, pBI101.2, and pBI101.3. Preferably, pBI101 and a vector derived therefrom can be used.

Examples of the pUC-type vector include pUC18, pUC19, and pUC9.

DNA containing an expression control region of a gene for an enzyme involved in a C4 pathway of photosynthesis and a structural gene for an enzyme involved in a C4 pathway of photosynthesis is linked into a vector by a method known to those skilled in the art. For example, in the case of using the pBI vector, the vector is digested with any one of appropriate restriction enzymes at a multi-cloning site, DNA of interest is inserted into the vector at the cleavage site, the resulting vector is transformed into an appropriate E. coli strain, a transformant is selected, and then an expression vector of interest is recovered.

Introduction of a Recombinant DNA Sequence or an Expression Vector into C3 Plant Cells Although not limited thereto, examples of the C3 plant to be transformed include rice, wheat, barley, soybeans, and potatoes. Plant cells from these plants can be prepared by a method known to those skilled in the art.

The recombinant DNA sequence or the expression vector is introduced via Agrobacterium or directly into a prepared plant cell. As the method using Agrobacterium, for example, a method of Nagel et al. (Microbiol. Lett. 67, 325 (1990)) can be used. According to this method, for example, Agrobacterium is first transformed with an expression vector by electroporation, and then transformed Agrobacterium is introduced into a plant cell by a method described in the Plant Molecular Biology Manual (S.B. Gelvin et al., Academic Press Publishers). As the method for directly introducing an expression vector into cells, an electroporation method and a gene gun method can be suitably used.

Regeneration of Transgenic Plant Cells into a Plant or a Plant Tissue

C3 plant cells in which a recombinant gene or an expression vector were introduced are subjected to a selection process based on drug resistance such as kanamycin resistance. Thereafter, the cells can be regenerated as a plant tissue or a plant by a conventional method, and seeds can be obtained from the plant. The seeds themselves may express the enzyme. Alternatively, the seeds may express an enzyme involved in a C4 pathway of photosynthesis only after they have germinated and begun to grow.

In order to confirm the expression of an enzyme involved in a C4 pathway of photosynthesis in the transgenic C3 plant, a method well known to those skilled in the art can be used. For example, the transformation and expression can be confirmed in accordance with an ordinary method by southern hybridization against DNA extracted from a plant tissue or plant leaf using a partial sequence of the introduced C4 photosynthesis gene as a probe, or by extracting a protein and measuring activity for the extracted protein from a plant tissue or plant leaf or subjecting the extracted protein to electrophoresis and subjecting a gel thus obtained to activity-staining.

$CO_2$ Compensation Point Measurement

The photosynthetic activity ($CO_2$ compensation point) of a transgenic plant can be measured using an ADC infrared gas analyzer, for example, in accordance with the description of Hudspeth et al., Plant Physiol. 98: 458–464 (1992). More specifically, a newly expanded leaf is sealed into a Plexiglass chamber. The temperature in the chamber is maintained at 30° C. $CO_2$ concentration is continuously measured by circulating the air through the chamber under illumination at a photosynthetically active photon flux density of 1000 $\mu mol/m^2/s$. The compensation point is determined when the $CO_2$ concentration inside the chamber reaches equilibrium.

Hereinafter, the present invention will be specifically described by exemplifying a maize PEPC genome gene as DNA containing an expression control region and a structural gene for an enzyme involved in a photosynthetic pathway of a C4 plant and rice as a C3 plant. It is to be appreciated that the present invention is not limited to the following examples. A restriction enzyme, plasmid, and the like used in the examples are available from Takara Shuzo Co., Ltd. and Toyobo Co., Ltd.

EXAMPLE 1

Isolation of a Maize PEPC Genome Gene

A maize PEPC genome gene was isolated by a method described in the literature (Eur. J. Biochem. 181: 593–598, 1989). Maize (*Zea mays* L. cv. Golden Cross Bantam) was planted in vermiculite. The planted maize was cultured in a culture chamber in darkness at 30° C. for 4 days. Genome DNA was isolated from etiolated leaves in accordance with a method of Matsuoka et al., Plant Physiol. 85: 942–946 (1987). This genome DNA was digested with XbaI and fractionated by 10% to 40% sucrose density gradient centrifugation. The obtained XbaI fragment was ligated to the XbaI arms of the phage λong C (Stratagene, Calif.) and the ligated DNA was packaged in vitro. The genomic library was constructed using the packaged DNA. Then, the phage plaques were screened by plaque hybridization using as a probe the sequence 5'-GTCCACGAGAAGATCCAGGG-3' described in Matsuoka et al., Plant Cell Physiol. 30: 479–486 (1989). cDNA clone (pPEP3055) isolated by using this probe can also be used as a probe. A positive clone was isolated, and the nucleotide sequence of the genomic clone was determined by a dideoxy method. About 8 Kb of XbaI—XbaI fragment containing the full-length PEPC structural gene was obtained. FIG. 1 shows a restriction map of a DNA fragment containing the obtained PEPC, and FIGS. 2 through 4 show the nucleotide sequence thereof.

The sequence of about 8 Kb of XbaI—XbaI fragment was analyzed to have an expression control region as shown in Table 1.

TABLE 1

| Element | Position | | Sequence |
|---|---|---|---|
| TATA box | −24 to −28 | | TATTT |
| CCAAT box | −367 to −371 | | CCAAT |
| SP-binding site | −80 to −85 | | CCGCCC |
| | −48 to −53 | | CCGCCC |
| | 275 to 280 | (intron 1) | CCGCCG |
| | 281 to 286 | (intron 1) | CCGCCC |
| Light responsive element | −653 to −661 | | CCTTATCCT |
| Direct repeat sequence | −536 to −550 | | CCCTCAACCACATCCTGC |
| | −510 to −527 | | GACACCCTCG-CCACATCC |
| | −453 to −470 | | GACGCCCTCT-CCACATCCTGC |
| | −378 to −395 | | GACGCCCTCT-CCACATCCTGC |
| | −201 to −214 | | CCCTCT-CCACATCC |
| | −30 to −39 | | CT-CCCCATCC |

EXAMPLE 2

Construction of an Expression Vector

Figure 5:
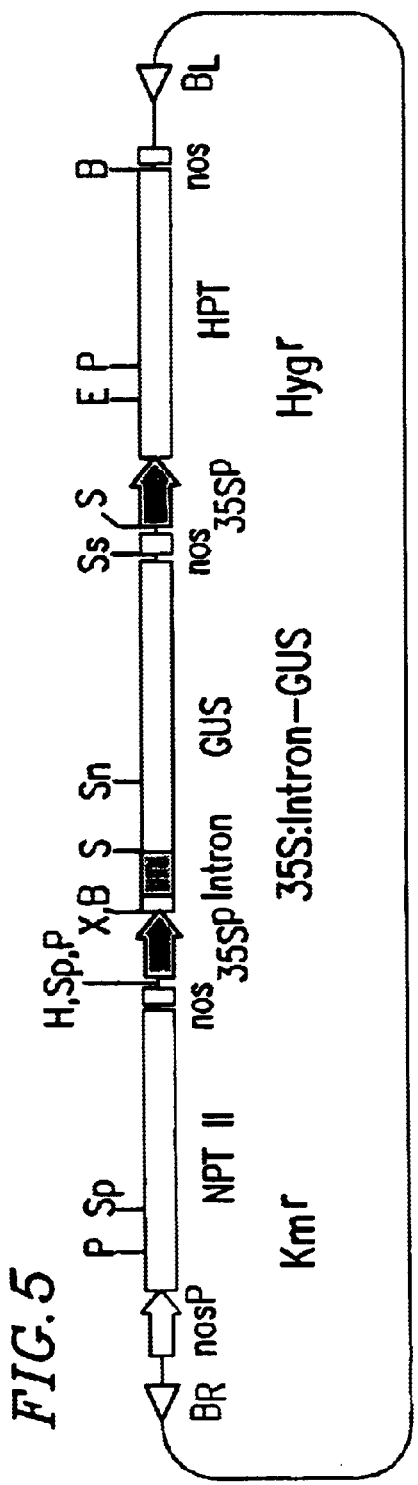
FIG. 5 is a diagram showing the binary vector pIG121-Hm.

The binary vector pIG121-Hm (FIG. 5) was constructed using pBI101(Jefferson et al., EMBO J. 6: 3901–3907 (1987), pIG221 (Ohta et al., Plant Cell Physiol. 31: 805–813 (1990), and pLAN101MHYG (provided by Dr. K. Shimamoto). This vector contains the NPTII gene controlled by the NOS promoter and terminator, multi-cloning sites, the β-GUS gene derived from *E. coli*, and the HPT gene with TNOS under the control of the 35S CaMV promoter.

Figure 6:
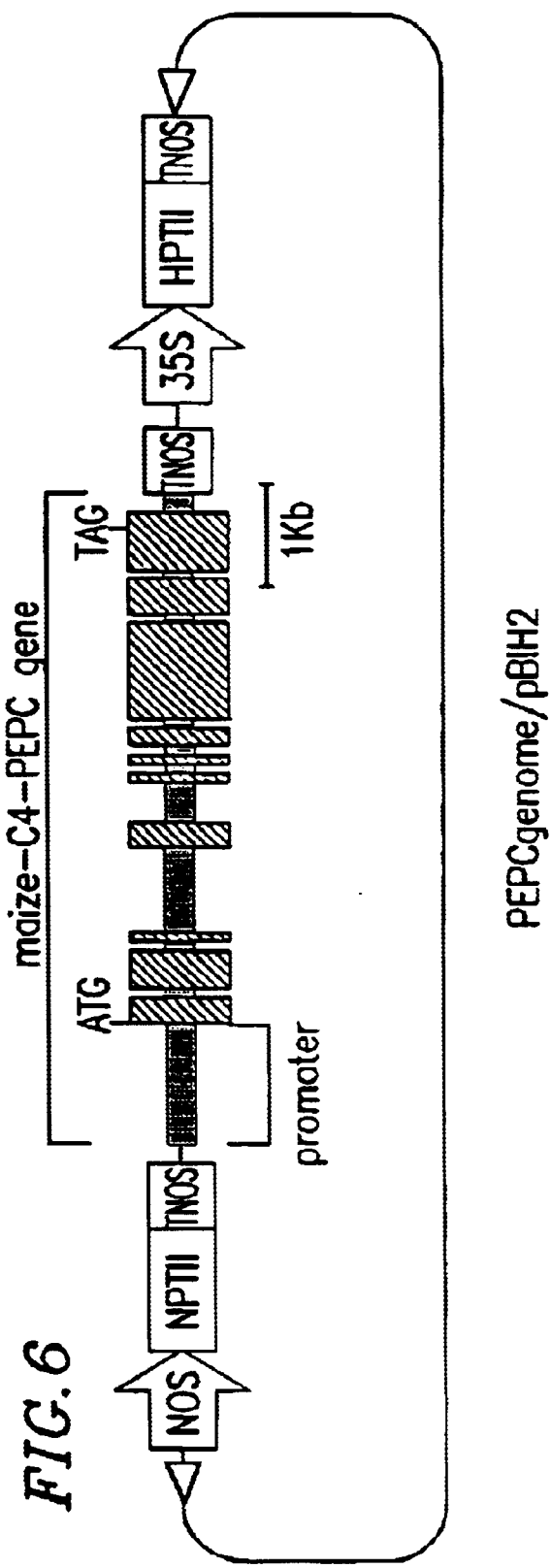
FIG. 6 is a diagram showing a structure of the expression vector PEPCgenome/pBIH2.

This vector pIG121-Hm was first digested with HindIII and SstI, and a large fragment was recovered. About 8 Kb of XbaI—XbaI fragment of the maize PEPC gene obtained in the above was linked to the digested vector, followed by being introduced into *E. coli* JM109. A kanamycin-resistant strain was recovered, and an expression vector PEPCgenome/pBIH2 in which the maize PEPC gene was introduced in a correct direction was found to be obtained by a restriction enzyme analysis (FIG. 6).

EXAMPLE 3

Introduction of the Expression Vector PEPCgenome/pBIH2 to Rice (Transformation of *Agrobacterium tumefaciens*)

*Agrobacterium tumefaciens* EHA101 (obtained from Dr. Nester of the University of Washington) was cultured at 28° C. in a culture medium containing 50 μg/ml of kanamycin and 100 μg/ml of hygromycine. A cell suspension culture was prepared, the expression vector PEPCgenome/pBIH2 was introduced into the above-mentioned bacterium by electroporation, and hygromycine-resistant strains were selected in accordance with a method of Nagel et al. (Micribiol. Lett., 67, 325 (1990)).

(Transformation of Rice Cells and Regeneration of Rice)

Agrobacterium transformed with an expression vector PEPCgenome/pBIH2 was obtained. Colonies were formed on an AB agar medium (Chilton et al., Proc. Natl. Acad. Sci. USA. 71: 3672–3676 (1974)). The resulting colonies were diluted with AAM medium (Hiei et al., Plant J. 6: 271–282 (1994)), and cocultivated with callus of rice (*Oryza sativa*) for 3 days. Thereafter, the bacterium was removed on a culture medium containing 50 μg/ml of hygromycine. The colonies were subcultured on a hygromycine selection culture medium every 2 weeks. The transgenic rice cells were selected and regenerated by a conventional method. As a result, 38 independent transgenic rice individuals were obtained.

EXAMPLE 4

Detection of Expression of the PEPC Gene in Transgenic Rice

The expression level of PEPC in 38 transgenic rice individuals thus obtained, non-transgenic rice, and maize were studied as follows. The PEPC activity was measured by a method described in Edwards et al., Aust. J. Plant Physiol. 15: 385–395 (1988). The PEPC enzyme was prepared in accordance with the description of Hudspeth et al., Plant Physiol. 98: 458–464 (1992). More specifically, about 0.5 g of green leaves were harvested, rapidly frozen with liquid nitrogen, and ground to fine powders. Ten-fold volume of an extraction buffer was added to the powders, and the powders were further ground. The extraction buffer contained 50 mM of Hepes-KOH (pH 8.0), 10 mM of $MgCl_2$, 1 mM of EDTA, 10 mM of DTT, 10% (w/v) insoluble PVP, 12.5% (v/v) glycerol, 10 μM of leupeptin, and 1 mM of PMSF. The crude extract was filtered with Miracloth (Calbiochem, La Jolla, Calif.). The filtrate was centrifuged at 4° C. and 15,000 rpm for 5 minutes, and the supernatant was desalted with Sephadex G-25 pre-equilibrated with a PVP-free extraction buffer. The eluate was pooled, and the enzyme activity and protein mass were measured.

Figure 7:
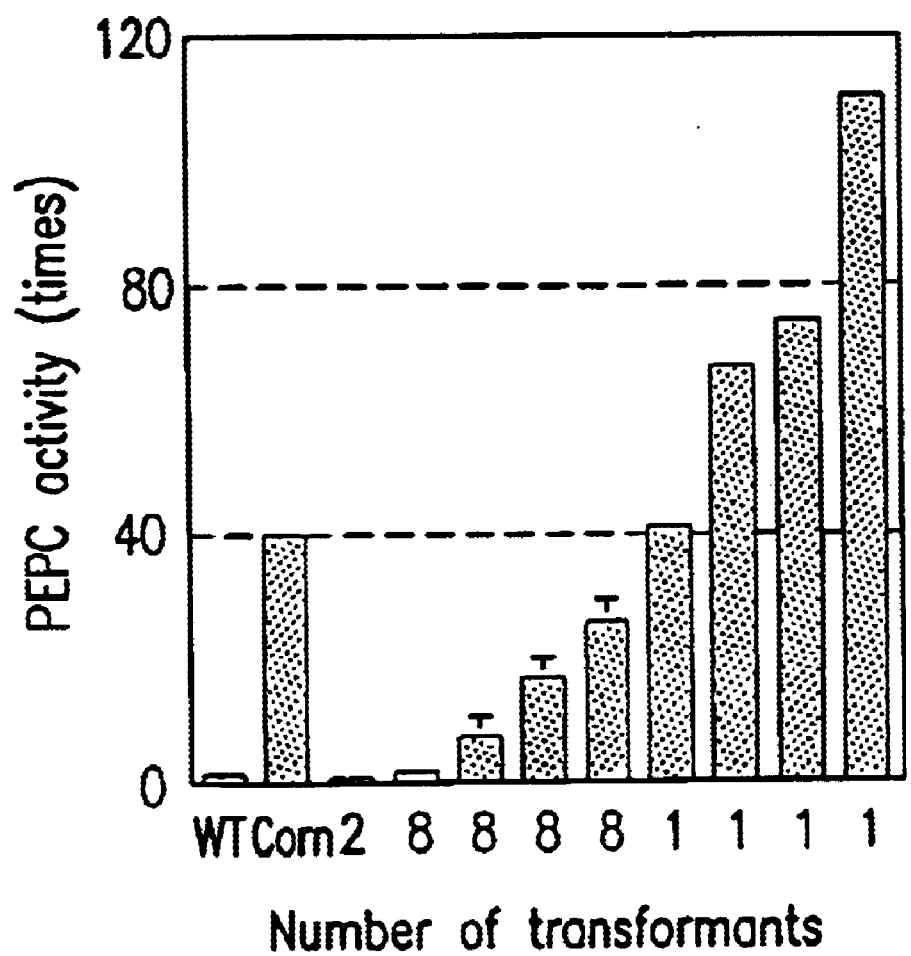
FIG. 7 is a diagram showing PEPC activities of transgenic rice plants.

FIG. 7 shows results. In FIG. 7, WT represents a wild-type, i.e., non-transgenic rice, and Corn represents maize. The PEPC activity was represented relatively, with the specific activity of PEPC in the crude extract from green leaves of non-transgenic rice being 1. Maize exhibited a PEPC activity about 40 times as high as that of the non-transgenic rice. Four out of 38 transgenic rice plants exhibited a PEPC activity higher than that of maize. Transgenic rice plants having a PEPC activity about 115 times as high as that of the non-transgenic rice were able to be obtained by transformation (the transgenic rice plants had a PEPC activity about 3 times as high as that of maize). It is surprising that the C3 poaceous plant with a genome gene of the C4 plant introduced therein exhibited a PEPC activity higher than that of the C4 plant.

EXAMPLE 5

$CO_2$ Compensation Point Measurements

The photosynthetic $CO_2$ compensation point was measured by using the non-transgenic rice and the transgenic rice having a PEPC activity about 75 times and about 7 times as high as that of the non-transgenic rice obtained in Example 4. Table 2 shows results.

TABLE 2

| Kind of rice | $CO_2$ compensation point (ppm) |
|---|---|
| Transgenic rice having a PEPC activity about 75 times as high as that of non-transgenic rice | 48.8 |
| Transgenic rice having a PEPC activity about 7 times as high as that of non-transgenic rice | 53.5 |
| Non-transgenic rice | 53.7 |

The transgenic rice having a PEPC activity about 75 times as high as that of the non-transgenic rice had its $CO_2$ compensation point decreased by about 10%. The further improvement of photosynthetic capacity is expected.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A C3 plant expressing a gene of a C4 plant of the same family, comprising DNA containing (a) an expression control region from maize phosphoenolpyruvate carboxylase (PEPC) or pyruvate orthophosphate dikinase (PPDK) genes and (b) a structural gene for the enzyme of the C4 plant, wherein the DNA is a nuclear genome gene of the C4 plant, wherein the enzyme encoded by the structural gene is selected from the group consisting of:

PEPC and PPDK from maize, and wherein the C3 plant expresses the enzyme encoded by the structural gene at a level the same as or higher than the expression in the C4 plant, and wherein the C3 plant is rice.

2. A method for producing a C3 plant which expresses a gene of a C4 plant of the same family, comprising the steps of:

transforming cells of the C3 plant with DNA containing (a) an expression control region from maize phosphoenolpyruvate carboxylase (PEPC) or pyruvate orthophosphate dikinase (PPDK) genes and (b) a structural gene for the enzyme of the C4 plant, wherein the DNA is a nuclear genome gene of the C4 plant and wherein the enzyme encoded by the structural gene is selected from the group consisting of:

PEPC and PPDK from maize; and regenerating the transformed cells of the C3 plant into the C3 plant; wherein the regenerated C3 plant expresses the enzyme encoded by the structural gene at a level the same as or higher than the expression in the C4 plant, and wherein the C3 plant is rice.

3. A C3 plant tissue expressing a gene of a C4 plant of the same family, comprising DNA containing (a) an expression control region from maize phosphoenolpyruvate carboxylase (PEPC) or pyruvate orthophosphate dikinase (PPDK) genes and (b) a structural gene for the enzyme of the C4 plant, wherein the DNA is a nuclear genome gene of the C4 plant, wherein the enzyme encoded by the structural gene is selected from the group consisting of:

PEPC and PPDK from maize, and wherein the C3 plant expresses the enzyme encoded by the structural gene at a level the same as or higher than the expression in the C4 plant, and wherein the C3 plant is rice.

4. A method for producing a C3 plant tissue which expresses a gene of a C4 plant of the same family, comprising the steps of:

transforming cells of the C3 plant with DNA containing (a) an expression control region from maize phosphoenolpyruvate carboxylase (PEPC) or pyruvate orthophosphate dikinase (PPDK) genes and (b) a structural gene for the enzyme of the C4 plant, wherein the DNA is a nuclear genome gene of the C4 plant, wherein the enzyme encoded by the structural gene is selected from the group consisting of: PEPC and PPDK from maize, and regenerating the transformed cells of the C3 plant into the C3 plant tissue; wherein the regenerated C3 plant tissue expresses the enzyme encoded by the structural gene at a level the same as or higher than the expression in the C4 plant, and wherein the C3 plant is rice.

5. A C3 plant seed expressing a gene of a C4 plant of the same family, comprising DNA containing (a) an expression control region from maize phosphoenolpyruvate carboxylase (PEPC) or pyruvate orthophosphate dikinase (PPDK) genes and (b) a structural gene for the enzyme of the C4 plant, wherein the DNA is a nuclear genome gene of the C4 plant, wherein the enzyme encoded by the structural gene is selected from the group consisting of:

PEPC and PPDK from maize, and wherein the C3 plant grown from the seed expresses the enzyme encoded by the structural gene at a level the same as or higher than the expression in the C4 plant, and wherein the C3 plant is rice.

6. A method for producing a C3 plant seed which expresses a gene of a C4 plant of the same family, comprising the steps of:

transforming cells of the C3 plant with DNA containing (a) an expression control region from maize phosphoenolpyruvate carboxylase (PEPC) or pyruvate orthophosphate dikinase (PPDK), genes and (b) a structural gene for the enzyme of the C4 plant, wherein the DNA is a nuclear genome gene of the C4 plant, wherein the enzyme encoded by the structural gene is selected from the group consisting of:

PEPC and PPDK from maize;

regenerating the transformed cells of the C3 plant into the C3 plant; and obtaining a seed from the C3 plant; wherein the C3 plant seed expresses, at least upon germination and growing, the enzyme encoded by the structural gene at a level the same as or higher than the expression in the C4 plant, and wherein the C3 plant is rice.

7. The C3 plant of claim 1, wherein the structural gene is PEPC.

8. The C3 plant of claim 1, wherein the structural gene is PPDK.

9. The method of claim 2, wherein the structural gene is PEPC.

10. The method of claim 2, wherein the structural gene is PPDK.

11. The C3 plant tissue of claim 3, wherein the structural gene is PEPC.

12. The C3 plant tissue of claim 3, wherein the structural gene is PPDK.

13. The method of claim 4, wherein the structural gene is PEPC.

14. The method of claim 4, wherein the structural gene is PPDK.

15. The C3 plant seed of claim 5, wherein the structural gene is PEPC.

16. The C3 plant seed of claim 5, wherein the structural gene is PPDK.

17. The method of claim 6, wherein the structural gene is PEPC.

18. The method of claim 6, wherein the structural gene is PPDK.

* * * * *